United States Patent [19]

Knell

[11] 4,013,621
[45] Mar. 22, 1977

[54] SUBSTITUTED SULFONAMIDE DERIVATIVES OF HINDERED PHENOLS AND STABILIZED COMPOSITIONS

[75] Inventor: Martin Knell, Ossining, N.Y.

[73] Assignee: Ciba-Geigy Corporation, Ardsley, N.Y.

[22] Filed: Apr. 29, 1975

[21] Appl. No.: 572,774

[52] U.S. Cl. .................. 260/45.9 R; 260/556 A; 260/556 AR; 260/556 S; 260/556 SN; 260/808

[51] Int. Cl.² .......................... C08K 5/42

[58] Field of Search ..... 260/556 A, 556 AR, 556 S, 260/556 SN, 45.9 R, 45.9 NC, 808

[56] References Cited

UNITED STATES PATENTS

| | | | |
|---|---|---|---|
| 2,093,947 | 9/1937 | Albrecht | 260/556 AR |
| 2,246,924 | 6/1941 | Paul | 260/808 |
| 2,352,950 | 7/1944 | Gates | 260/556 AR |
| 2,359,360 | 10/1944 | Gibbs | 260/808 |
| 3,004,035 | 10/1961 | Csendes | 260/808 |
| 3,496,211 | 2/1970 | Dexter et al. | 260/45.9 R |
| 3,507,825 | 4/1970 | Paris | 260/45.9 R |
| 3,754,031 | 8/1973 | Dexter et al. | 260/808 |
| 3,790,526 | 2/1974 | Brindell et al. | 260/45.9 R |
| 3,847,960 | 11/1974 | Avar et al. | 260/45.9 R |

OTHER PUBLICATIONS

Chemistry and Industry, Feb. 16, 1963, by Scott, pp. 271–281.

S. I. Burmistov and N. P. Smolyakova, Zh. Organ Khim, I(2), 286, (1965).

S. I. Burmistov and L. G. Romanovskaya, Zh. Organ Khim, I(2), 321, (1965).

*Primary Examiner*—V. P. Hoke
*Attorney, Agent, or Firm*—Luther A. R. Hall

[57] ABSTRACT

A compound of the formula

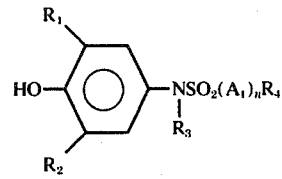

wherein $R_1$ and $R_2$ are each independently alkyl of 1 to 8 carbon atoms or cycloalkyl of 5 to 6 carbon atoms, $R_3$ is hydrogen, lower alkyl of 1 to 4 carbon atoms or the group $—SO_2(A_2)_nR_5$, $R_4$ and $R_5$ are each independently alkyl of 1 to 18 carbon atoms or cycloalkyl of 5 to 12 carbon atoms, providing that $R_4$ and $R_5$ may each independently be hydrogen when $n$ is 1, $A_1$ and $A_2$ are each independently phenyl, 1-naphthyl, 2-naphthyl, 2-(5,6,7,8-tetrahydro)naphthyl or p-phenylene, and $n$ is 0 or 1 is prepared by reaction of a sulfonyl halide and a 2,6-substituted-4-aminophenol.

The compounds are particularly effective in stabilizing unsaturated elastomeric compositions against oxidative degradation.

18 Claims, No Drawings

SUBSTITUTED SULFONAMIDE DERIVATIVES OF HINDERED PHENOLS AND STABILIZED COMPOSITIONS

DETAILED DISCLOSURE

This invention pertains to para-substituted sulfonamides of hindered phenols and to organic materials normally subject to oxidative and thermal degradation stabilized with said sulfonamides.

More specifically the compounds of this invention are those having the formula

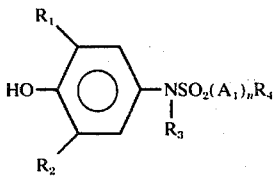

wherein
- $R_1$ and $R_2$ are each independently alkyl of 1 to 8 carbon atoms, cycloalkyl of 5 to 6 carbon atoms, benzyl, α-methylbenzyl or α,α-dimethylbenzyl,
- $R_3$ is hydrogen, lower alkyl of 1 to 4 carbon atoms or the group $-SO_2(A_2)_nR_5$,

- $R_4$ and $R_5$ are each independently alkyl of 1 to 18 carbon atoms or cycloalkyl of 5 to 12 carbon atoms, providing that $R_4$ and $R_5$ may each be independently hydrogen when $n$ is 1,
- $A_1$ and $A_2$ are each independently phenyl, 1-naphthyl, 2-naphthyl, 1-(5,6,7,8-tetrahydro)naphthyl, 2-(5,6,7,8-tetrahydro)naphthyl, or p-phenylene, and
- $n$ is 0 or 1.

The $R_1$ and $R_2$ groups can be straight or branched chain alkyl groups of 1 to 8 carbons such as methyl, ethyl, isopropyl, tert-butyl, tert-amyl, n-octyl or tert-octyl. $R_1$ and $R_2$ can also be cycloalkyl of 5 to 6 carbon atoms such as cyclopentyl or cyclohexyl. $R_1$ and $R_2$ can also be benzyl, α-methylbenzyl or α,α-dimethylbenzyl.

Preferably $R_1$ and $R_2$ are each independently alkyl of 1 to 4 carbon atoms such as methyl, ethyl, isopropyl and tert-butyl. Most preferably $R_1$ and $R_2$ are each tert-butyl.

$R_3$ can be hydrogen or lower alkyl of 1 to 4 carbon atoms such as methyl, ethyl, n-propyl or n-butyl. $R_3$ can also be the group $-SO_2(A_2)_nR_5$.

Preferably $R_3$ is hydrogen, methyl or $-SO_2(A_2)_nR_5$. More preferably $R_3$ is hydrogen.

The $R_4$ and $R_5$ groups can be straight or branched chain alkyl of 1 to 18 carbon atoms such as methyl, ethyl, isopropyl, n-butyl, isobutyl, tert-butyl, tert-amyl, n-octyl, n-dodecyl, tert-dodecyl, n-hexadecyl or n-octadecyl.

The $R_4$ and $R_5$ groups can also be cycloalkyl of 5 to 12 carbon atoms such as cyclopentyl, cyclohexyl, or cyclododecyl.

When $n$ is 1, $R_4$ and $R_5$ can also each independently be hydrogen.

When $n$ is 0 or 1, preferably the $R_4$ and $R_5$ groups are each independently alkyl of 1 to 12 carbon atoms such as methyl, ethyl, n-butyl, n-octyl or n-dodecyl. Preferably $R_4$ and $R_5$ can each independently be cycloalkyl of 6 to 12 carbon atoms such as cyclohexyl or cyclododecyl. When $n$ is 1, $R_4$ and $R_5$ can also preferably each independently be hydrogen.

Most preferably when $n$ is 0, $R_4$ and $R_5$ can independently be methyl or n-octyl. Most preferably when $n$ is 1, $R_4$ and $R_5$ can independently be hydrogen, methyl, n-octyl, n-dodecyl, cyclohexyl or cyclododecyl.

The groups $A_1$ and $A_2$ are each independently phenyl, 1-naphthyl, 2-naphthyl, 1-(5,6,7,8-tetrahydro)naphthyl, 2-(5,6,7,8-tetrahydro)naphthyl or p-phenylene.

Preferably $A_1$ and $A_2$ are each independently phenyl, 2-(5,6,7,8-tetrahydro)naphthyl or p-phenylene.

Most preferably $A_1$ and $A_2$ are each p-phenylene.

The sulfonamides of this invention where $R_3$ is hydrogen are prepared by reacting the appropriately substituted 4-aminophenol with a sulfonyl halide preferably in the presence of an acid acceptor to neutralize the acid formed during the reaction. This reaction is outlined below.

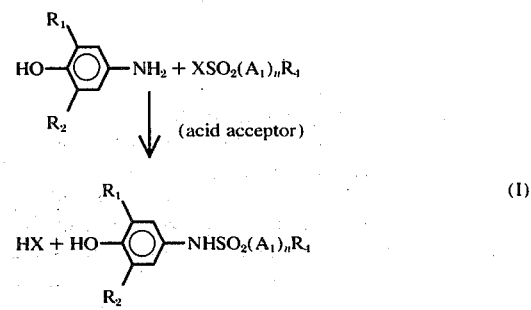

(I)

X can be chlorine or bromine, but preferably, for reasons of economy and availability, it will be chlorine. The reaction can be carried out in any inert solvent such as acetone, chloroform, benzene or toluene. The preferred acid acceptor is aqueous sodium hydroxide although any base stronger than the substituted 4-aminophenol can be used.

The alkanesulfonyl or cycloalkanesulfonyl halides are made by one of several methods preferably from the corresponding mercaptan by oxidation with halogens.

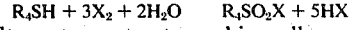

Alternate routes to making alkanesulfonic acids involve reaction of the corresponding alkyl halide with sodium sulfite or the oxygen-induced anti-Markownikoff addition of sodium bisulfite to an alkene.

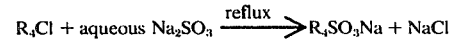

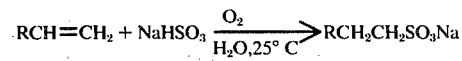

($RCH_2CH_2$ is $R_4$)

The resulting sulfonic acid or sodium sulfonate can be converted to the sulfonyl chloride by reaction with thionyl chloride, phosphorus pentachloride or the like.

The sulfonamides of this invention where $R_3$ is alkyl or the group $-SO_2(A_2)_nR_5$ are made by further reaction of the sulfonamide of Formula I with either an alkylating agent such as methyl iodide, dimethyl sulfate or n-butyl bromide or an additional amount of the same or a different sulfonyl halide in the presence of a base.

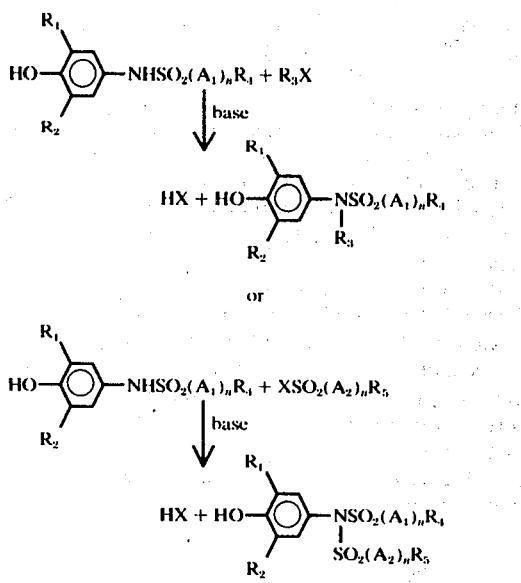

where X is chlorine or bromine.

The substituted 4-aminophenols useful in making the sulfonamides of this invention are in turn made using the general teachings of U.S. Pat. No. 3,255,191, the disclosures of which are herein incorporated by reference. The general method employed involves the nitrosation of various 2,6-dialkylphenols using sodium nitrite followed by reduction with reducing agents such as sodium hydrosulfite to prepare the substituted 2,6-dialkyl-4-aminophenols.

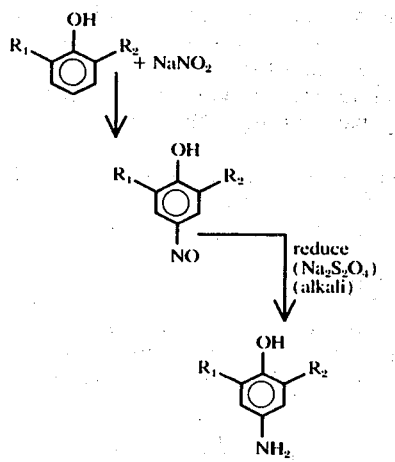

Many of the 2,6-dialkylphenols are items of commerce such as 2-methyl-6-tert-butylphenol, 2,6-dimethyl phenol and 2,6-di-tert-butylphenol. Other 2,6-dialkylphenols can be made by the aluminum phenoxide catalyzed alkylation of phenol or o-alkylphenol using the appropriate olefin such as isobutylene, styrene, 2 methyl-1-butene, 2,4,4-trimethyl-1-pentene, cyclohexene and the like.

The sulfonyl halides useful in making the sulfonamides of this invention are in some cases items of commerce. Among such intermediates are benzenesulfonyl chloride, p-toluenesulfonyl chloride, 2-naphthalenesulfonyl chloride, methanesulfonyl chloride and n-hexadecanesulfonyl chloride.

Other sulfonyl halides useful as intermediates can be conveniently made by one of several methods outlined below.

An alkylbenzene or alkylnaphthalene can easily be chlorosulfonated as seen in Example 4 using chlorosulfonic acid in an inert solvent.

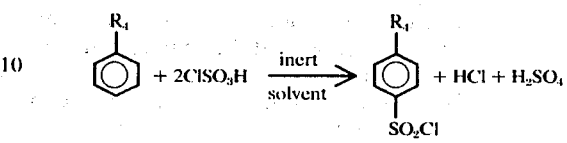

The sulfonamide derivatives of hindered phenols of this invention are stabilizers of organic material normally subject to thermal and oxidative deterioration. Materials which are thus stabilized include synthetic organic polymeric substances such as poly-α-olefins, polyethylene, polypropylene, crosslinked polyethylene, polybutylene including copolymers of α-olefins such as ethylene/propylene copolymer; dienes such as polybutadiene, polyisoprene, and the like, including copolymers with other monomers; polyurethanes and polyamides such as polyhexamethylene adipamide and polycaprolactam; polyesters such as polyethylene terephthalates; polycarbonates; polyacetals; unsaturated polyesters; polystyrene, polyethylene oxide; and copolymers such as those of high impact polystyrene containing copolymers of butadiene and styrene and those formed by the copolymerization of acrylonitrile, butadiene and/or styrene, ABS; SAN; natural and synthetic rubbers such as ethylene/propylene/diene copolymer (EPDM) and chlorinated rubber; polyphenylene oxide and copolymers; vinyl resins formed from the polymerization of vinyl halides or from co-polymerization of vinyl halides with unsaturated polymerizable compounds, e.g., vinyl esters, α,β-unsaturated ketones, α,β-unsaturated aldehydes and unsaturated hydrocarbons such as butadienes and styrene; and plasticized polyvinyl chloride.

Other materials which can be stabilized by the compounds of the present invention include lubricating oil of the aliphatic ester type, i.e., di(2-ethylhexyl)azelate and other synthetic ester lubricants, pentaerythritol tetracaproate, and the like; spinning lubricants of the polyester type; animal and vegetable derived oils, e.g., linseed oil, fat, tallow, lard, peanut oil, cod liver oil, castor oil, palm oil, corn oil, cottonseed oil, and the like; hydrocarbon materials such as gasoline, mineral oil, fuel oil, drying oil, mineral lube oils, cutting fluids, waxes, resins and the like, salts of fatty acids such as soaps and the like; and alkylene glycols, e.g., β-methoxyethylene glycol, methoxytriethylene glycol, triethylene glycol, octaethylene glycol, dibutylene glycol, dipropylene glycol and the like.

The substrates of particular importance are the unsaturated elastomers such as polybutadiene, polyisoprene, styrene/butadiene copolymer rubber, chloroprene rubber, nitrile rubbers and the like. Polybutadiene, polyisoprene, SBR rubbers and copolymers containing as one component butadiene or isoprene are especially well stabilized by the compounds of this invention.

The compounds of this invention where $R_3$ is hydrogen are particularly effective stabilizers for these unsaturated elastomers.

In general, the stabilizers of this invention are employed from about 0.01 to about 5% by weight of the stabilized composition, although this will vary with the particular substrate and application. An advantageous range is from about 0.05 to about 2% and especially from about 0.1 to about 1%.

For addition to polymeric substrates, the stabilizers can be blended before polymerization or after polymerization, during the usual processing operations, for example, by dry blending, extruder compounding and hot-milling. The composition then can be extruded, pressed, injected molded or otherwise fabricated into films, fibers, filaments, molded items and the like. The heat stabilizing properties of these compounds advantageously stabilize the polymer against degradation during such processing at the high temperature generally encountered. However, the useful life of polymeric materials is also extended by these stabilizers far beyond their ability to survive processing.

The stabilizers can also be dissolved in suitable solvents and sprayed on the surface of films, fabrics, filaments or the like to provide effective stabilization.

These compounds can also be used in combination with other additives such as sulfur-containing esters, e.g., distearyl $\beta$-thiodipropionate (DSTDP) in an amount of from 0.01 to 2% by weight of the organic material, and the like, pourpoint depressants, corrosion and rust inhibitors, dispersing agents, emulsifiers, antifoaming agents, carbon black, accelerators and other chemicals used in rubber compounding, plasticizers, color stabilizers, antistatic agents, antislip agents, antiblock agents, surface active agents, fillers, organophosphites, organothiophosphites, heat stabilizers, ultraviolet light stabilizers, anti-ozonants, dyes, pigments, metal deactivators, metal chelating agents, dyesites and the like. Often combinations such as these, particularly the sulfur containing esters, the phosphites and/or the ultraviolet light stabilizers will produce superior results in certain applications to those expected by the properties of the individual components.

The following formula represents co-stabilizers which are in certain instances very useful in combination with the stabilizers of this invention:

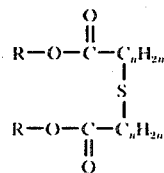

wherein R is an alkyl group having from 6 to 24 carbon atoms; and $n$ is an integer from 1 to 6. Especially useful compounds of this type are dilauryl $\beta$-thiodipropionate and distearyl $\beta$-thiodipropionate. The above co-stabilizers are used in the amount of from 0.01 to 2% by weight of the organic material, and preferably from 0.1 to 1%.

In addition to the above noted additives that can be employed in combination with the compounds of this invention, it is often especially advantageous to employ also light stabilizers. The light stabilizers are used in the amount of from 0.01 to 5% by weight of the organic material, and preferably from 0.1 to 1%. Illustrative examples of light stabilizers are listed below.

UV-Absorbers and light protection agents 2-(2'-hydroxyphenyl)-2H-benzotriazoles, such as, for example, the 5'-methyl-; 3', 5'-di-tert.-butyl-; 5'-tert.-butyl-; 5'-(1,1,3,3-tetramethylbutyl)-; 5-chloro-3', 5'-tert.-butyl-; 5-chloro-3'-tert.-butyl-5'-methyl-; 3'-sec.-butyl-5'-tert.-butyl-; 3'-[α-methylbenzyl]-5'methyl-5-chloro-; 4'-hydroxy-; 4'-methoxy-; 4'-octoxy-; 3',5'-di-tert.-amyl-; 3'-methyl-5'-carbomethoxyethyl-; 5-chloro-3', 5'-di-tert.-amyl-or 4'-tert-octyl- derivatives.

2,4-bis-(2'-hydroxyphenyl)-6-alkyl-s-triazines, such as, for example, the 6-ethyl-, 6-undecyl- or 6-heptadecyl- derivatives.

2-hydroxybenzophenones, such as, for example, the 4-hydroxy-, 4-methoxy-, 4-octoxy-, 4-decyloxy, 4-dodecyloxy-, 4-benzyloxy-, 4,2',4'-trihydroxy- or 2'-hydroxy-4,4'-dimethoxy- derivatives.

1,3-bis-(2'-hydroxybenzoyl)benzenes, such as for example, 1,3-bis-(2'-hydroxy-4'-hexyloxybenzoyl)-benzene, 1,3-bis-(2'-hydroxy-4'-octoxybenzoyl)benzene and 1,3-bis-(2'-hydroxy-4'dodecyloxybenzoyl)-benzene.

Esters of optionally substituted benzoic acids, such as, for example, phenyl salicylate, octylphenyl salicylate, dibenzoylresorcinol, bis-(4-tert.-butyl-benzoyl)-resorcinol, benzoylresorcinol, 3,5-di-tert.-butyl-4-hydroxybenzoic acid 2,4-di-tert.butylphenyl ester, octadecyl ester or 2-methyl-4,6-di-tert.-butylphenyl ester, and alkyl esters of 4-(3,5-di-tert-butyl-4-hydroxybenzoyloxy)-3,5-di-tert-butylbenzoic acid.

Acrylates, such as, for example, α-cyano-β,β-diphenylacrylic acid ethyl ester or isooctyl ester, α-carbomethoxycinnamic acid methyl ester, α-cyano-β-methyl-p-methoxycinnamic acid methyl ester or butyl ester and N-(β-carbomethoxy-vinyl)-2-methylindoline.

Nickel compounds, such as, for example, nickel complexes of 2,2'-thio-bis-4-(1,1,3,3-tetramethylbutyl)-phenol, such as the 1:1 and 1:2 complex, optionally with other ligands such as n-butyl-, triethanol-, cyclohexylor N-cyclohexyldiethanolamine; nickel complexes of bis-[2-hydroxy-5-(1,1,3,3-tetramethylbutyl)-phenyl]sulfone, such as the 2:1 complex, optionally with other ligands such as 2-ethylcaproic acid; nickel dibutyldithiocarbamate, nickel salts of 4-hydroxy-3,5-di-tert.-butylbenzyl-phosphonic acid monoalkyl esters, such as the methyl, ethyl or butyl ester, the nickel complex of (2-hydroxy-4-methylphenyl)undecylketonoxime and nickel 3,5-di-tert.-butyl-4-hydroxybenzoate.

Oxalic acid diamides, such as, for example, 4,4'-dioctyloxyoxanilide, 2,2'-dioctyloxy-5,5'-di-tert.-butyloxanilide, 2,2'-didodecyloxy-5,5'-di-tert-butyloxanilide, 2-ethoxy-5-tert-butyl-2'-ethyloxanilide, 2-ethoxy-2'-ethyloxanilide, N,N'-bis-(3-dimethylaminopropyl)oxalamide, mixtures of o- and p-methoxy and o- and p-ethoxy-di-substituted oxanilides and mixtures of 2-ethoxy-5-tert.-butyl-2'-ethyloxanilide with 2-ethoxy-2'-ethyl-5,4'-di-tert.-butyloxanilide.

Sterically hindered amines, such as, for example, 4-benzoyloxy-2,2,6,6-tetramethylpiperidine, 4-stearoyloxy-2,2,6,6-tetramethylpiperidine, bis-(2,2,6,6-tetramethylpiperidyl) sebacate and 3-n-octyl-7,7,9,9-tetramethyl-1,1,3,8-triazaspiro[4,5]decan-2,4-dione.

For exemplification purposes only, below are listed compounds of this invention which are useful as stabilizers as discussed above:

2,6-di-tert-octyl-4-(p-toluenesulfonamido)phenol
2,6-di-tert-amyl-4-(p-toluenesulfonamido)phenol
2-methyl-6-tert-butyl-4-(p-toluenesulfonamido)phenol
2,6-dicyclohexyl-4-(p-toluenesulfonamido)phenol 2,6-di-tert-butyl-4-(n-dodecanesulfonamido)phenol
2,6-di-tert-butyl-4-cyclododecanesulfonamidophenol
2,6-di-tert-octyl-4-cyclohexanesulfonamidophenol
2,6-di-tert-amyl-4(N-ethyl-p-n-octylbenzenesulfonamido)phenol
2,6-di-tert-butyl-4(N-n-butyl-cyclohexanesulfonamido)phenol
2,6-di-tert-butyl-4-(bis-n-dodecanesulfon)amidophenol
2,6-di-tert-octyl-4-(bis-methanesulfon)amidophenol
2,6-di-tert-butyl-4-benzenesulfonamidophenol
2,6-di-tert-butyl-4-(naphthalene-2-sulfonamido)-phenol
2,6-di-tert-octyl-4-(naphthalene-1-sulfonamido)-phenol
2,6-di-tert-butyl-4-(bis-p-toluenesulfon)amidophenol
2-6-di-tert-amyl-4-(N-benzenesulfonyl-p-toluenesulfonamido)phenol The following examples are illustrative of the invention, but are not meant to limit the scope of the same in any fashion.

EXAMPLE 1

2,6-Di-tert-butyl-4-(p-toluenesulfonamido)phenol a. 4-Nitroso-2,6-di-tert-butylphenol Ethanol (75 ml) was cooled to 15° C and saturated with hydrogen chloride gas. This solution was diluted by addition of another 400 ml of ethanol. To this alcoholic solution was added 82.4 grams of 2,6-di-tert-butylphenol. After it was dissolved, a solution of 30.4 grams of sodium nitrite in 40 ml of water was added at 15°-20° C over a period of one hour with stirring. Stirring was continued for another two hours with the temperature allowed to rise to room temperature. The solution was diluted with 200 ml of water, and the product formed was collected by filtration and washed well with water. The filter cake was then slurried in 300 ml of petroleum ether, filtered, washed with another 100 ml of petroleum ether and dried in a vacuum oven at 70°-80° C to yield the desired intermediate 4-nitroso-2,6-di-tert-butylphenol, melting at 219° C.

b. 4-Amino-2,6-di-tert-butylphenol

To 17.6 grams of 4-nitroso-2,6-di-tert-butylphenol dissolved in 60 ml of 5N sodium hydroxide and 120 ml of water was added with stirring over a 30-minute period a solution of 52.2 grams of sodium hydrosulfite in 220 ml of water during which time the temperature rose to 53° C. After the addition was complete, stirring was continued for another 2.5 hours. The product formed was then rapidly collected by filtration, washed with 400 ml of water and dried in a vacuum desiccator over phosphorus pentoxide to yield 4-amino-2,6-di-tert-butylphenol, melting at 105°-108° C.

c. 2,6-Di-tert-butyl-4-(p-toluenesulfonamido)phenol

To a solution of 11.05 grams (0.05 mole) of 4-amino-2,6-di-tert-butylphenol in 50 ml of acetone was added with mixing 9.5 grams (0.05 mole) of p-toluenesulfonyl chloride. After the slight exotherm subsided, 10 ml of 5N sodium hydroxide solution was added. During this addition, an oil separated which eventually solidified. An additional 50 ml of water was added, and the product was separated by filtration. The crude product weighed 12.88 grams and melted at 160°-180° C. After recrystallization from methanol/water and ethanol/water, the melting point was 180°-182° C. (Compound 1)

Calc'd for $C_{21}H_{29}NO_3S$: C, 67.16; H, 7.78. Found: C, 66.94; H, 7.81.

EXAMPLE 2

2,6-Di-tert-butyl-4-methanesulfonamidophenol

To a solution of 11.05 grams (0.05 mole) of 4-amino-2,6-di-tert-butylphenol in 60 ml of chloroform was added with stirring 5.75 grams (0.05 mole) of methanesulfonyl chloride over a 5-minute period. The reaction mixture was heated to 35° C for 15 minutes followed by the dropwise addition of 8.0 grams (0.05 mole) of a 25% aqueous sodium hydroxide solution and finally heating at 47° C for 30 minutes. After cooling to room temperature, the chloroform layer was separated, washed with water and dried over 4A Molecular Sieves and filtered. The solvent was removed in vacuo, and the residue was washed with hexane leaving 5.8 grams of a crude pink product. Recrystallization from toluene and again from ethylene dichloride gave 2.7 grams of colorless crystals melting at 149°-151° C. (Compound 2)

Calc'd for $C_{15}H_{25}NO_3S$: C, 60.17; H, 8.42: N, 4.68: S, 10.71. Found: C, 60.15; H, 8.31; N, 4.70; S, 10.64.

EXAMPLE 3

2,6-Di-tert-butyl-4-(n-octanesulfonamido)phenol and 2,6-Di-tert-butyl-4-(bis-n-octanesulfon)amidophenol To a solution of 6.6 grams (0.03 mole) of 4-amino-2,6-di-tert-butylphenol in 50 ml of benzene was added with stirring 6.4 grams (0.03 mole) of n-octanesulfonyl chloride over a 20-minute period. After the exothermic reaction which raised the temperature to 27° C subsided, 3.0 grams (0.03 mole) of triethylamine was added dropwise over a 10-minute period raising the temperature to 46° C. Stirring was continued for 1 hour without external heating after which the benzene solution was washed well with water, dried over Molecular Sieves 4A and filtered. The solvent was removed in vacuo, and the resulting residue was washed well with hexane leaving 5.8 grams of a white solid. Recrystallization of the crude white solid from 60 ml of hot heptane gave 4.8 grams of white crystals shown by NMR and elemental analysis to be 2,6-di-tert-butyl-4-(n-octanesulfonamido)phenol and melting at 106°-109° C. (Compound 3)

Calc'd for $C_{22}H_{39}NO_3S$: C, 66.45; H, 9.89; N, 3.52; S, 8.06. Found: C, 66.42; H, 9.62; N, 3.60; S, 7.94.

The hexane washings from the isolation of the monosulfonamido product above were evaporated to dryness leaving a residue of 4.8 grams. The residue was triturated with warm hexane and filtered leaving 0.8 gram of insoluble material. This insoluble material was then recrystallized from 10 ml of hot heptane to give 0.45 gram of a compound shown by NMR and elemental analysis to be 2,6-di-tert-butyl-4-(bis-n-octanesulfon)amidophenol, melting at 126°-129° C. (Compound 4)

Calc'd for $C_{30}H_{55}NO_5S_2$: C, 62.78; H, 9.66; N, 2.44; S, 11.18. Found: C, 62.73; H, 9.57; N, 2.40; S, 11.19.

EXAMPLE 4

2,6-di-tert-butyl-4(p-n-dodecylbenzenesulfonamido)-phenol a. p-n-Dodecylbenzenesulfonyl Chloride To a solution of 24.6 grams (0.1 mole) of n-dodecylbenzene in 150 ml of carbon tetrachloride was added with stirring 34.8 grams (0.3 mole) of chlorosulfonic acid over a 1-hour period. The reaction was exothermic with the temperature rising to 27° C. Stirring was continued for 4 hours after which the reaction mixture was carefully poured onto 1 liter of cracked ice with vigorous stirring. Chloroform (200 ml) was added and the aqueous layer was saturated with sodium chloride. The chloroform layer was separated, washed two times with 500 ml of saturated aqueous sodium chloride solution, dried over Molecular Sieves 4A and filtered. The solvent was removed in vacuo, and the resulting residue was recrystallized from 100 ml of hexane. The dried product weighed 22.6 grams and melted at 33°–35° C.

b. 2,6-Di-tert-butyl-4(p-n-dodecylbenzenesulfonamido)phenol

To a solution of 4.4 grams (0.02 mole) of 4-amino-2,6-di-tert-butylphenol in 25 ml of toluene was added with stirring 6.8 grams (0.02 mole) of p-n-dodecylbenzenesulfonyl chloride followed by the dropwise addition of 3.2 grams (0.02 mole) of 25% aqueous sodium hydroxide solution. After the exothermic reaction which raised the temperature to 33° C was over, stirring was continued for several hours. The toluene layer was then separated, washed with water, dried over Molecular Sieves 4A and filtered. The toluene was removed in vacuo and the resulting residue was recrystallized from 50 ml of hot hexane giving 7.5 grams of a pink product melting at 79°–83° C. Another recrystallization from hexane give 6.6 grams of white crystals melting at 81°–83° C. (Compound 5)

Calc'd for $C_{32}H_{51}NO_3S$: C, 72.54; H, 9.70; N, 2.64; S, 6.05. Found: C, 72.90; H, 9.60; N, 2.59; S, 6.07.

EXAMPLE 5

2,6-Di-tert-butyl-4(N-methyl-p-toluenesulfonamido)phenol

To a solution of 3.75 grams (0.01 mole) of the product of Example 1, 2,6-di-tert-butyl-4(p-toluenesulfonamido)phenol, and 0.54 grams (0.01 mole) of sodium methylate in 50 ml of methanol was added 1.42 grams (0.01 mole) of methyl iodide. The reaction mixture was heated with stirring for 72 hours in a pressure tube at 100° C. The reaction mixture was then cooled, poured into 150 ml of water and extracted with heptane. The heptane layer was separated and allowed to stand after cooling. Crystals formed which were isolated by filtration, washed and dried to weigh 0.5 gram and melted at 123°–142° C. Recrystallization from heptane gave 0.2 gram of crystals melting at 130°–142° C. Proton NMR spectra confirmed the expected, desired structure. (Compound 6)

Calc'd for $C_{22}H_{31}NO_3S$: C, 67.83; H, 8.02; N, 3.60; S, 8.23. Found: C, 67.73; H, 8.07; N, 3.49; S, 8.29.

EXAMPLE 6

2,6-Di-tert-butyl-4-(p-cyclohexylbenzenesulfonamido)phenol a. p-Cyclohexylbenzenesulfonyl Chloride By following the procedure described in Example 4 a), when an equivalent amount of cyclohexylbenzene was substituted for n-dodecylbenzene, p-cyclohexylbenzenesulfonyl chloride was prepared. After removing the solvent, the crude product solidified on cooling and had a melting point of 42°–52° C. Elemental and TLC analyses indicated the crude product was of adequate purity for use in the next step in the synthesis.

b. 2,6-Di-tert-butyl-4(p-cyclohexylbenzenesulfonamido)phenol

When using the procedure described in Example 4 (b) an equivalent amount of p-cyclohexylbenzenesulfonyl chloride was substituted for p-n-dodecylbenzenesulfonyl chloride, the desired product was obtained which after crystallization from isopropanol/water melted at 155°–157° C. (Compound 7)

Calc'd for $C_{26}H_{37}NO_3S$: C, 70.39; H, 8.41; N, 3.16; S, 7.23. Found: C, 70.21; H, 8.43; N, 3.06; S, 7.14.

EXAMPLE 7

2,6-Di-tert-butyl-4(5,6,7,8-tetrahydronaphthalene-2-sulfonamido)phenol

When using the procedure described in Example 4 b) an equivalent amount of 5,6,7,8-tetrahydronaphthalene-2-sulfonyl chloride, prepared by the procedure of Huntress and Autenrieth, *J. Amer. Chem. Soc.*, 63, 3446 (1941), was substituted for p-n-dodecylbenzenesulfonyl chloride, the desired product was obtained which after crystallization from isopropanol/water melted at 129°–133° C. (Compound 8)

Calc'd for $C_{24}H_{33}NO_3S$: C, 69.36; H, 8.00; N, 3.37; S, 7.72. Found: C, 69.02; H, 7.92; N, 3.28; S, 7.55.

EXAMPLE 8

2,6-Di-tert-butyl-4(p-cyclododecylbenzenesulfonamido)phenol a. p-Cyclododecylbenzenesulfonyl Chloride When following the procedure described in Example 4 (a), n-dodecylbenzene was replaced by an equivalent amount of cyclododecylbenzene, p-cyclododecylbenzenesulfonyl chloride was obtained as a crude product of adequate purity for the next synthetic step.

b. 2,6-Di-tert-butyl-4(p-cyclododecylbenzenesulfonamido)phenol

When using the procedure described in Example 4 (b), p-n-dodecylbenzenesulfonyl chloride was replaced by an equivalent amount of p-cyclododecylbenzenesulfonyl chloride, the desired product was obtained which after crystallization from isopropanol/water and recrystallization from heptane melted at 174°–176° C. (Compound 9)

Calc'd for $C_{32}H_{49}NO_3S$: C, 72.73; H, 9.35; N, 2.65; S, 6.07. Found: C, 72.32; H, 8.95; N, 2.62; S, 6.06.

EXAMPLE 9

Stabilization of Polybutadiene

Using a Brabender Plasticorder operated at 50 rpm and at 100° C under a nitrogen atmosphere, the stabilizers of this invention were incorporated into as-received polybutadiene rubber ("Solprene" 201, Phillips Petroleum) in 4-minute incorporation periods. The compounded material was then compression molded into 25 mil (0.635 mm) thick plaques at 110° C for 1 minute at 1000 psi (70 kg/cm²) and 4 minutes at 6000 psi (420 kg/cm²) in a hydraulic press. Specimens measuring 2.5 inches × 1.25 inches (6.3 cm × 3.15 cm) were placed on aluminum sheets and oven aged at 100° C for various intervals at which time Gardner color readings were taken.

Gel content determinations were also made by preparing a 0.5% solution by weight of the aged rubber in toluene. After filtering through a fritted glass filter, two 10 ml aliquots of the filtrate were dried and the rubber residue weighed. The percent gel in the rubber was calculated according to the formula $$\% \text{ Gel} = \frac{100 (W_i - 10W_f)}{W_i}$$

where $W_i$ is the weight of aged rubber in 100 ml of toluene, i.e., 0.5 gram, and $W_f$ is the weight of the rubber residue.

The effectiveness of the antioxidant stabilizers may be seen in the length of time of oven aging at 100° C that is required before any gel is observed in the oven aged sample as well as by the prevention of undue color formation during said aging.

The results are set forth in Table I.

Table I

| | Oven Aging of Polybutadiene at 100° C | | | | | | |
|---|---|---|---|---|---|---|---|
| 0.125% by Weight Stabilizer | Hours to Onset of Gel | Gardner* Color After Hours of 100° C Oven Aging | | | | | |
| | | 0 | 40 | 80 | 120 | 160 | 200 | 240 |
| None | 2 | | | | | | | |
| Solprene 201** | 5 | 0 | 9 | 10 | 10 | 11 | 11+ | |
| Compound 1 | 193 | | | | | | | |
| Compound 2 | 75 | 0 | 1 | 3 | 9 | 10 | 10 | 11 |
| Compound 3 | 186 | 0 | 1 | 2 | 2 | 2 | 3 | 9 |
| Compound 4 | 20 | 0 | 9 | 10 | 11 | 11 | 11+ | |
| Compound 5 | 155 | 0 | 1 | 2 | 2 | 3 | 9 | 11+ |
| Compound 6 | 50 | 0 | 6 | 9 | 10 | * Low 11+ | | |
| BHT (1%) | 10 | | | | | | | |
| Polygard (1.25%) | 10 | | | | | | | |

* Low Gardner color numbers mean low discoloration.
**"Solprene" 201 is believed to contain 0.75% BHT and 0.5% "Polygard".
BHT is 2,6-di-tert-butyl-4-methylphenol
Polygard is tri(nonylphenyl)phosphite In polybutadiene rubber, as well as in SBR, the onset of decomposition is accompanied by crosslinking. Thus, the measurement of time required to observe incipient gel formation is a rapid and reliable evaluation tool for measuring the efficacy of stabilizers for these polymers.

The sulfonamides of this invention are particularly effective in protecting polybutadiene against oxidative degradation as seen by a long delay in the onset of gel formation. The compounds of this invention having a free hydrogen on the sulfonamide nitrogen are especially preferred and effective.

EXAMPLE 10

Stabilization of Thermoplastic SBR

Using a Brabender Plasticoder operated at 150° C under a nitrogen atmosphere, the stabilizers of this invention were incorporated into as-received thermoplastic styrene/butadiene rubber (SBR) (Kraton 1101, Shell) in 3-minute incorporation periods. 25 mil (0.635 mm) plaques made as described in Example 9 and weighing about 1 gram each were oven agen at 90° C in a forced draft oven. Toluene insoluble gel measurements and Hunter (L-b) color measurements were made periodically. The Hunter values were obtained using a Hunter Lab Color Difference Meter in the usual manner. The L values are the measure of whiteness and the b values of yellowness. The higher the L-b value, the whiter is the sample. The percent gel was calculated as seen in Example 9. The results are set forth in Table II.

Table II

| | Oven Aging of Thermoplastic SBR at 90° C | | | | | |
|---|---|---|---|---|---|---|
| 0.2% by Weight Stabilizer | Hours to Onset of Gel | Hunter (L-b) Values After Hours of Oven Aging | | | | |
| | | 0 | 20 | 50 | 100 | 230 |
| "Kraton*" 1101 | 2 | 82 | 66 | 53 | 47 | 40 |
| Compound 1 | 140 | 80 | 78 | 71 | 60 | 46 |

*"Kraton" 1101 is believed to contain 0.2% BHT, 2,6-di-tert-butyl-4-methylphenol.

The sulfonamides of this invention are very effective antioxidant stabilizers in protecting thermoplastic SBR rubber from oxidative degradation as seen by the long period before any gel formation is observed in oven aged SBR containing the instant sulfonamide.

The sulfonamides of this invention also protect thermoplastic SBR rubber from discoloration effectively as seen from the Hunter (L-b) Values.

EXAMPLE 11

Stabilization of Polyisoprene

Using a Brabender Plasticorder operated at 90° C under a nitrogen atmosphere, the stabilizers of this invention were incorporated into as-received polyisoprene rubber, (Ameripol SN-600, B. F. Goodrich) in 4-minute incorporation periods. 25 mil (0.635 mm) plaques prepared as in Example 9 were oven aged at 70° C in a forced draft oven. Whereas polybutadiene and SBR rubbers crosslink and form gel on oven aging, polyisoprene rubber undergoes chain scission on oven aging thus becoming soft and tacky. Thus, the time in days required for the specimen to become sticky (to the touch) and the specimen Gardner color were taken as the criteria of onset of decomposition and efficiency of the stabilizers present to prevent said decomposition. The results are set forth in Table III.

Table III

| | Oven Aging of Polyisoprene at 70° C | | | | |
|---|---|---|---|---|---|
| 0.1% by Weight Stabilizer | Days to Exhibit Stickiness | Gardner* Color After Days | | | |
| | | 0 | 6 | 20 | 31 |
| None | 2 | 0 | 4 | 7 | 8 |
| Ameripol** SN-600 | 3 | 0 | 0 | 7 | 8 |
| Compound 1 | 14 | 0 | 0 | 1 | 1 |

Table III-continued

Oven Aging of Polyisoprene at 70° C

| 0.1% by Weight Stabilizer | Days to Exhibit Stickiness | Gardner* Color After Days | | | |
|---|---|---|---|---|---|
| | | 0 | 6 | 20 | 31 |
| BHT** (1.5%) | 3 | 0 | 0 | 7 | 8 |

* Low Gardner colors mean low discoloration.
** Ameripol SN-600 as received contains some BHT, 2,6-di-tert-butyl-4-methylphenol.

The sulfonamides of this invention are very effective in preventing the discoloration and oxidative degradation of polyisoprene.

EXAMPLE 12

Unstabilized linear polyethylene (HiFax 4401) is solvent blended in methylene chloride with 0.2 by weight of the substrate of 2,6-di-tert-amyl-4-(N-n-butyl-cyclohexanesulfonamido)phenol and then vacuum dried. The resin is then extruded at 450° F (232.2° C) using a ¾ inch (1.905 cm) extruder having a 24:1 L/D ratio. The melt flow rate of a sample of the resin is determined after each extrusion according to ASTM test D-1238. Polyethylene stabilized with above compound is found to undergo less change in the melt flow rate than the unstabilized polyethylene.

EXAMPLE 13

To 50 g of polyacetal resin containing 0.1% of an acid scavenger, dicyandiamide, is added 0.2% by weight of 2,6-di-tert-butyl-4-benzenesulfonamidophenol and milled for 7 minutes at 200° C in a Brabender Plasticorder. The milled formulation is subsequently pressed into a 40 mil (1.016 mm) sheet at 215° C at 350 psi (24.5 kg/cm²) for 90 seconds then cooled quickly in a cold press at 350 psi (24.5 kg/cm²). The stabilized sheets are then remolded for 2 minutes at contact pressure and for 3 minutes at 300 psi (21 kg/cm²) at 215° C to give plaques 1.5 × 1.5 inch × 125 mil (3.81 cm × 5.715 cm × 3.175 mm). The plaques are aged in the oven at 60° C and the weight loss of the specimen is determined periodically until a 4% weight loss is reached. The stabilized sample takes a much longer time to reach this 4% weight loss than does the unstabilized sample.

EXAMPLE 14

Unstabilized, thoroughly dried polyethylene terephthalate chips are dry blended with 1.0% by weight of 2,6-di-tert-octyl-4-(bis-methanesulfon)amidophenol. 60/10 denier multifilament is melt spun at a melt temperature of 290° C and cold oriented 3 to 1. The oriented fibers are wound into skeins and oven aged at 140° C. The stabilized material exhibits greater retention of tensile strength after 24 hours than the unstabilized material.

EXAMPLE 15

A stabilized high temperature lubricating oil is prepared by incorporating 0.05% by weight of 2,6-di-tert-octyl-4-(bis-n-dodecanesulfon)amidophenol to the lubricant which comprises diisoamyl adipate. The stabilized composition is compared with the unstabilized lubricant by heating at 175° C in the presence of air and metallic catalysts according to the test method described in Military Specification Mil-I-7808c. After 72 hours, the blank containing no stabilizer contains more sludge and has a greater viscosity than the stabilized lubricant.

EXAMPLE 16

Unstabilized polypropylene powder (Hercules Profax 6501) was thoroughly blended with 0.5% by weight of Compound 1. The blended materials were then milled on a two-roll mill at 182° C for 10 minutes after which time the stabilized polypropylene was sheeted from the mill and allowed to cool.

The milled polypropylene sheets were then cut into pieces and pressed for 7 minutes on a hydraulic press at 218° C and 275 psi (19.25 kg/cm²) pressure. The resulting plaques of 25 mil (0.635 mm) thickness were tested for resistance to accelerated aging in a forced draft oven at 150° C. When the plaques showed the first signs of decomposition (e.g., cracking or brown edges), they were considered to have failed.

Without any stabilizer, the polypropylene plaques failed after 3 hours of oven aging at 150° C. With 0.5% by weight of Compound 1, the plaques did not fail until after 23 hours of oven aging at 150° C.

EXAMPLE 17

Pellets (500 g) of unstabilized nylon-6,6 (Zytel 101, DuPont) are placed in a Kitchen Aid Mixer. With mixing a solution of 0.5% (based on the weight of nylon) of 2,6-di-tert-octyl-4-(p-toluenesulfonamido)phenol in 20 ml of methylene chloride is added slowly. Sodium hypophosphite (0.5 gm 0.14) is dissolved in 20 ml of water and added slowly with mixing to the nylon pellets after the antioxidant solution has been added and most of the methylene chloride has evaporated. The stabilized pellets are dried at 80° C at <<1 mm Hg. for 4 hours.

The polyamide formulation is extruded at 600° F (315.6° C) through a ¼ inch (0.635 cm) die into a rod which is water cooled and chopped into pellets. A ¾ inch (1.905 cm) Brabender extruder, equipped with a nylon screw, is used. The pellets are dried at 80° C at <1 mm for 4 hours.

The dried pellets are compression molded into 5 mil (0.127 mm) thick film by pressing at 290° C for 4 minutes at 6000 psi (57.75 kg/cm²). The films are oven aged at 150° C in a forced draft oven and samples are removed periodically. The specific viscosity of the samples are determined using a 1% formic acid solution at 25° C. The sample stabilized with the above noted stabilizer required longer aging time to reduce its viscosity by one-half than the unstabilized sample.

EXAMPLE 18

Unstabilized high impact polystyrene resin is dry blended with 0.01% by weight of the resin of 2,6-di-tert-butyl-4-cyclododecanesulfonamidophenol. The resin is then extrusion compounded on a 1 inch (2.54 cm) 24/1=L/D extruder, melt temperature 500° F (260° C) and pressed for 7 minutes at a temperature of 163° C and a pressure of 2000 psi (140 kg/cm²) into a sheet of uniform thickness of 100 mil (2.54 mm). The sheets are then cut into plaques of 2 inch × 2 inch (5.08 cm × 5.08 cm). The plaques are then oven agen at 80° C and color measurements made periodically using a Hunter Color Difference Meter Model D25. The polystyrene samples stabilized with the above stabilizer develops the undesirable yellow discoloration substantially later than the time that such discoloration occurred in the unstabilized samples.

What is claimed is:

1. A compound of the formula

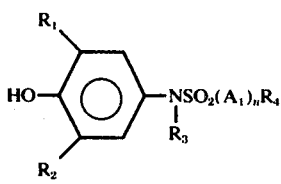

wherein
R₁ and R₂ are each tert-butyl,
R₃ is hydrogen, lower alkyl of 1 to 4 carbon atoms or the group

—SO₂(A₂)ₙR₅,

R₄ and R₅ are each independently alkyl of 1 to 18 carbon atoms or cycloalkyl of 5 to 12 carbon atoms, providing that R₄ and R₅ may each be independently hydrogen when n is 1,
A₁ and A₂ are each independently phenyl, 1-naphthyl, 2-naphthyl, 1-(5,6,7,8-tetrahydro)naphthyl, 2-(5,6,7,8-tetrahydro)naphthyl or p-phenylene, and
n is 0 or 1.

2. A compound according to claim 1 wherein R₁ and R₂ are each tert-butyl, R₃ is hydrogen, methyl or the group —SO₂(A₂)ₙR₅, R₄ and R₅ are each independently alkyl of 1 to 12 carbon atoms or cycloalkyl of 6 to 12 carbon atoms, providing when n is 1, R₄ and R₅ may each independently be hydrogen, A₁ and A₂ are each independently phenyl, 2-(5,6,7,8-tetrahydro)-naphthyl or p-phenylene, and n is 0 or 1.

3. A compound according to claim 1 wherein R₁ and R₂ are each tert-butyl, R₃ is hydrogen, R₄ and R₅ can be independently, when n is 0, methyl or n-octyl; or when n is 1, hydrogen, methyl, n-octyl, n-dodecyl, cyclohexyl or cyclododecyl, A₁ and A₂ are each p-phenylene, and n is 0 or 1.

4. A compound according to claim 3 wherein R₁ and R₂ are each tert-butyl, R₃ is hydrogen, R₄ and R₅ are each independently methyl or n-octyl, and n is 0.

5. A compound according to claim 3 wherein R₁ and R₂ are each tert-butyl, R₃ is hydrogen, R₄ and R₅ are each independently hydrogen, methyl, n-octyl, n-dodecyl, cyclohexyl or cyclododecyl, A₁ and A₂ are each p-phenylene, and n is 1.

6. A compound according to claim 1 wherein R₃ is hydrogen.

7. The compound according to claim 1 which is 2,6-di-tert-butyl-4-(p-toluenesulfonamido)phenol.

8. The compound according to claim 1 which is 2,6-di-tert-butyl-4-(n-octanesulfonamido)phenol.

9. The compound according to claim 1 which is 2,6-di-tert-butyl-4-(p-n-dodecylbenzenesulfonamido)phenol.

10. The compound according to claim 1 which is 2,6-di-tert-butyl-4-(5,6,7,8-tetrahydronaphthalene-2-sulfonamido)phenol.

11. The compound according to claim 1 which is 2,6-di-tert-butyl-4-(p-cyclododecylbenzenesulfonamido)phenol.

12. A composition of matter comprising an olefinic polymer subject to degradation and from 0.01 to 5% by weight of a stabilizing compound of claim 1.

13. A composition according to claim 12 wherein the stabilizing compound is 2,6-di-tert-butyl-4-(p-toluenesulfonamido)phenol.

14. A composition according to claim 12 wherein the olefinic polymer is an unsaturated elastomer.

15. A composition according to claim 14 wherein the unsaturated elastomer is polybutadiene.

16. A composition according to claim 14 wherein the unsaturated elastomer is polyisoprene.

17. A composition according to claim 14 wherein the unsaturated elastomer is a copolymer rubber containing butadiene.

18. A composition according to claim 14 wherein the unsaturated elastomer is a copolymer rubber containing isoprene.

* * * * *